United States Patent
Schulz

(10) Patent No.: US 11,981,621 B2
(45) Date of Patent: May 14, 2024

(54) METHOD FOR OPERATING A PLANT FOR SYNTHESIZING METHANOL

(71) Applicants: GASCONTEC GMBH, Bad Homburg v. d. Höhe (DE); THYSSENKRUPP INDUSTRIAL SOLUTIONS AG, Essen (DE)

(72) Inventor: Alexander Schulz, Frankfurt (DE)

(73) Assignees: GASCONTEC GMBH, Bad Homburg V. D. HÖNE (DE); THYSSENKRUPP UHDE GMBH, Dortmund (DE)

( * ) Notice: Subject to any disclaimer, the term of this patent is extended or adjusted under 35 U.S.C. 154(b) by 396 days.

(21) Appl. No.: 17/425,816

(22) PCT Filed: Jan. 24, 2020

(86) PCT No.: PCT/EP2020/051715
§ 371 (c)(1),
(2) Date: Jul. 26, 2021

(87) PCT Pub. No.: WO2020/152311
PCT Pub. Date: Jul. 30, 2020

(65) Prior Publication Data
US 2022/0162142 A1    May 26, 2022

(30) Foreign Application Priority Data

Jan. 25, 2019 (EP) .................................. 19153767.9

(51) Int. Cl.
*C07C 29/152* (2006.01)
*B01J 19/24* (2006.01)

(52) U.S. Cl.
CPC ......... *C07C 29/152* (2013.01); *B01J 19/2465* (2013.01)

(58) Field of Classification Search
CPC .... C07C 29/152; C07C 31/04; B01J 19/2465; Y02P 20/129
See application file for complete search history.

(56) References Cited

FOREIGN PATENT DOCUMENTS

| EP | 0123534 A2 | 10/1984 |
| EP | 3205622 A1 | 8/2017 |
| WO | 2013158343 A1 | 10/2013 |

OTHER PUBLICATIONS

International Search Report dated Apr. 28, 2020 re: Application No. PCT/EP2020/051715, pp. 1-2, citing: EP 0123534 A2, WO 2013158343 A1 and EP 3205622 B1.

*Primary Examiner* — Jafar F Parsa
(74) *Attorney, Agent, or Firm* — CANTOR COLBURN LLP

(57) ABSTRACT

A method for operating a plant for synthesizing methanol, wherein a synthesis gas flow having hydrogen and carbon oxides is supplied to a synthesis gas compressor of the plant to increase the pressure of the synthesis gas flow. The pressure-increased synthesis gas flow is supplied to a methanol reactor arrangement of the plant for partial conversion to methanol. The plant has a hydrogen recovery arrangement which obtains an H-recycling flow including hydrogen from a recovery flow supplied from the methanol reactor arrangement, which hydrogen is converted at least in part to methanol. Upon failure of the synthesis gas compressor, the synthesis gas flow continues to be supplied to the methanol reactor arrangement for partial conversion to methanol. Following failure of the synthesis gas compressor, a line arrangement of the plant is switched such that the H-recycling flow is adjusted to compensate for a pressure loss in the methanol reactor arrangement.

15 Claims, 7 Drawing Sheets

METHOD FOR OPERATING A PLANT FOR SYNTHESIZING METHANOL

TECHNICAL FIELD

The disclosure relates to a method for operating a plant for synthesizing methanol and a plant for synthesizing a hydrogen-containing compound according to the preamble of the independent claims.

BACKGROUND

Methanol is produced regularly in a plurality reactor stages of a plant for synthesizing methanol, which reactor stages are connected in series in terms of process technology, to which reactor stages a synthesis gas flow comprising hydrogen and carbon oxides is supplied and in which the exothermic reaction for the production of methanol takes place.

Such a plant for the production of methanol is known from EP 3 205 622 81, from which the present disclosure is based as the closest. From this prior art, it is particularly known to allow said reaction to take place in an increased pressure range in the reactor stages in order to enable an economical reaction of the methanol synthesis. Said increased pressure range can be achieved in that the synthesis gas flow experiences a pressure increase through a compressor, the synthesis gas compressor.

Since the synthesis gas does not undergo complete conversion to methanol in a single pass through the reactor stages and the gas supplied to the reactor stages also does not consist entirely of hydrogen and carbon oxides, there remains a residual gas in addition to the methanol formed, which in addition to unreacted hydrogen and carbon oxides and methane, can also contain the inert components nitrogen and noble gases. Provision is therefore made for the residual gas to be returned to the reactor stages for synthesizing methanol on the one hand, after the crude methanol has been separated off and to recycle said residual gas in this way and, on the other hand, to remove part of the gas from said synthesis cycle as purge gas in order to particularly prevent an accumulation of the inert components in the circuit.

In order to limit the loss of usable constituents of the residual gas, here especially hydrogen, when removing the purge gas, a hydrogen-containing gas, which can still be used as fuel gas, is separated from the residual gas before the remaining part of the residual gas is removed as purge gas. Said recovery of hydrogen is also important because, in this way, the stoichiometry of the gas in the reactors can be adjusted for synthesizing methanol.

One component of such a plant for synthesizing methanol that is prone to failure is the compressor for the synthesis gas. If such a failure occurs, the plant can usually no longer be operated for synthesizing methanol. This is not only due to the fact that the synthesis gas to be compressed directly by the synthesis gas compressor no longer has the pressure required for methanol synthesis due to the failure. It is also due to the fact that the hydrogen-containing gas from the hydrogen recovery no longer has the required pressure for supply. Without the gas from the hydrogen recovery, however, the stoichiometric number targeted in normal operation cannot be achieved either.

SUMMARY

Based on this prior art, the object of the disclosure is therefore to improve and further develop the method known from the prior art for operating a plant for synthesizing methanol and the plant known from the prior art for synthesizing methanol so that further operation is possible even if the synthesis gas compressor fails.

In relation to a method for operating a plant for synthesizing methanol according to the preamble of claim 1, this object is achieved by the features of the characterizing part of claim 1. In relation to a plant for synthesizing methanol according to the preamble of claim 15, this object is achieved by the features of the characterizing part of claim 15.

The disclosure is based on the knowledge that a plant for synthesizing methanol can basically continue to operate even after a failure of the synthesis gas compressor by adjusting the flow comprising the recovered hydrogen to compensate for the failure of the synthesis gas compressor. Although a reduction in the throughput of the plant can also be expected as a result of such an adjustment, said reduction is less pronounced. The adjustment of the flow comprising the recovered hydrogen can particularly take place such that the result is that the hydrogen in the flow comprising the recovered hydrogen is supplied to the reactor stages at a higher pressure than without said adjustment. The adjustment can take place specifically in that the supply of the gas for hydrogen recovery and, alternatively or additionally, the supply of the recovered hydrogen is changed by switching in the direction thereof and thus in the course thereof. On the one hand, the supply can be changed such that gas is supplied to the hydrogen recovery at a higher pressure from the start. On the other hand, the recovered hydrogen can also be supplied to the reactor stages such that it experiences a pressure increase after the change. In this way, the negative effect of the failure of the synthesis gas compressor is at least in part mitigated and the plant for synthesizing methanol can continue to be operated.

The proposed method is used to operate a plant for synthesizing methanol. In the proposed method, a synthesis gas flow comprising hydrogen and carbon oxides is supplied to a synthesis gas compressor of the plant to increase the pressure of the synthesis gas flow. The synthesis gas flow thus comprises hydrogen, carbon monoxide and carbon dioxide and can particularly also comprise other components such as nitrogen and noble gases. Likewise, in the method according to the proposal, the pressure-increased synthesis gas flow is supplied to a methanol reactor arrangement in the plant for partial conversion to methanol. The feature of the partial conversion to methanol is based on the fact that an unconverted residue of starting materials emerges from the methanol reactor arrangement and therefore the conversion does not take place completely.

In the proposed method, the plant has a hydrogen recovery arrangement which obtains an H-recycling flow comprising hydrogen from a recovery flow supplied by the methanol reactor arrangement. In the proposed method, said hydrogen is at least in part converted to methanol. Said partial conversion to methanol particularly takes place in that at least part of the hydrogen in the H-recycling flow is returned directly or indirectly to the methanol reactor arrangement and reacts there to form methanol. As is described below, said supply of the hydrogen to the methanol reactor arrangement can take place indirectly such that the hydrogen is supplied to the methanol reactor arrangement as part of a series of further flows.

The proposed method is characterized in that upon failure of the synthesis gas compressor, the synthesis gas flow continues to be supplied to the methanol reactor arrangement for partial conversion to methanol.

The proposed method is further characterized in that following failure of the synthesis gas compressor, a line arrangement of the plant is switched such that the H-recycling flow is adjusted to compensate for a pressure loss in the methanol reactor arrangement. Said adjustment of the H-recycling flow can relate to the composition thereof, the pressure thereof and, alternatively or additionally, the course thereof. The switching of the line arrangement of the plant means that basically any flow in the plant is directed differently after the switching than before the switching, said switching directly or indirectly causing the adjustment of the H-recycling flow. Particularly, switching the line arrangement can mean that the flow in question is directed through a first sub-line of the line arrangement before the switching and, after the switching, said flow is directed through a second sub-line of the line arrangement. The second sub-line is then different from the first sub-line and has a different course, for example.

The actual process of switching can, in principle, take place any time after the failure of the synthesis gas compressor and, in principle, also before an expected failure of the synthesis gas compressor. A deliberate shutdown of the synthesis gas compressor is equivalent to an unintentional failure of the synthesis gas compressor. The reason for the failure of the synthesis gas compressor is therefore irrelevant. The switching can also affect more than one line arrangement and thus a plurality of line arrangements. Particularly, switching can change the direction of a plurality of flows.

In principle, the partial conversion of the pressure-increased synthesis gas flow in the methanol reactor arrangement can take place over a wide pressure range. However, it is particularly advantageous to provide the synthesis gas flow at the highest possible pressure. It is therefore preferred that upon failure of the synthesis gas compressor and after the line arrangement has been switched, the synthesis gas flow is supplied to the methanol reactor arrangement at a pressure of at least 40 bar and particularly at a pressure of at least 50 bar. In this way, it is ensured that the methanol synthesis takes place following failure of the synthesis gas compressor in a pressure range which allows the plant to be operated economically despite a reduced throughput.

In addition to the compressor for the particularly fresh synthesis gas, a plant for synthesizing methanol can have at least one further compressor, also referred to as a recycle compressor, which compresses unreacted residual gas from the methanol reactors for return to the methanol reactors. Correspondingly, a preferred embodiment of the method is characterized in that a residual gas flow comprising unreacted residual gas is obtained from the methanol reactor arrangement and that the plant has a recycle compressor for increasing the pressure of the residual gas flow and for supplying the pressure-increased residual gas flow to the methanol reactor arrangement for partial conversion to methanol. The methanol reactor arrangement preferably comprises a methanol separation device for obtaining the unreacted residual gas and a crude methanol flow. In principle, the methanol separation device can function in any way. Particularly, it can be that the methanol separation device comprises a condensation device for obtaining the unreacted residual gas and the crude methanol flow by condensation.

In principle, it can be that the methanol reactor arrangement comprises only a single methanol reactor stage. A further preferred embodiment of the method is characterized in that the methanol reactor arrangement has a plurality of reactor stages for methanol synthesis which are connected in series in terms of process technology. Each individual reactor stage can have one or more reactors. The reactors of a reactor stage can particularly be arranged in parallel with one another in terms of process technology.

The fact that the reactor stages are connected in series in terms of process technology means that residual gas from one reactor stage, provided it is not the last reactor stage in the series of reactor stages, is supplied directly or indirectly to each subsequent reactor stage. In principle, the above recycle compressor can be arranged as desired with regard to the plurality of reactor stages. One variant is that the recycle compressor is arranged between two reactor stages in terms of process technology. This means that at least part of a gas from a reactor stage is supplied to the recycle compressor and the pressure-increased residual gas flow is then supplied to the reactor stage downstream of said reactor stage.

According to a preferred embodiment of the method, it is provided that the pressure-increased synthesis gas flow is supplied to a first reactor stage of the plurality of reactor stages. It is further preferred that the residual gas flow is obtained from a reactor stage downstream of the first reactor stage in terms of process technology. In other words, the residual gas flow supplied to the recycle compressor does not come from the first reactor stage, that is, the reactor stage to which the synthesis gas flow is supplied directly, but from a downstream reactor stage. It can also be that the recycle compressor supplies the pressure-increased residual gas flow to the first reactor stage. In principle, however, the increased residual gas flow can also be supplied to another reactor stage of the plurality of reactor stages.

In principle, the H-recycling flow can be directed as desired, as long as at least part of the hydrogen thereof is converted to methanol. According to a further preferred embodiment of the method, it is preferred in this regard that, after the line arrangement has been switched, the H-recycling flow is supplied to the unreacted residual gas. In other words, the hydrogen of the H-recycling flow is treated together with at least part of the unreacted residual gas after the supply. It is further preferred here that after the line arrangement has been switched, the H-recycling flow together with the residual gas flow is supplied to the recycle compressor to increase the pressure. The H-recycling flow can then experience a pressure increase through the recycle compressor, which compensates for the lack of pressure increase caused by the synthesis gas compressor following failure of the synthesis gas compressor.

The switching can therefore affect the course of the H-recycling flow. Switching can also affect the course of other flows. Thus, a preferred embodiment of the method is characterized in that the course of the recovery flow is changed by switching the line arrangement. This is because the recovery flow is preferably branched off from the unreacted residual gas before the line arrangement is switched. Said branching-off can particularly take place upstream of the recycle compressor in terms of process technology. In such a case, the branched-off recovery flow did not experience the pressure increase caused by the recycle compressor, which is why it makes sense to increase the pressure of the H-recycling flow through the synthesis gas compressor.

Conversely, if the synthesis gas compressor fails, it is then advantageous to achieve a pressure increase for the recovery flow, so that the H-recycling flow also indirectly has a higher pressure. A further preferred embodiment of the method is therefore characterized in that the switching of the line arrangement supplies the recovery flow to the hydrogen recovery arrangement at an increased pressure. By switching the line arrangement, the recovery flow is preferably supplied at a higher pressure than before the switching of the line arrangement, particularly being supplied to the hydrogen recovery arrangement. A preferred option for increasing the pressure of the recovery flow is to have said recovery flow previously compressed by the recycle compressor. Accordingly, it is preferred that after the line arrangement has been switched, the recovery flow is branched off from the residual gas flow downstream of the recycle compressor in terms of process technology.

According to a preferred embodiment of the method, the course of the H-recycling flow is changed by switching the line arrangement. Preferably, before the line arrangement is switched, the H-recycling flow is supplied to the synthesis gas flow upstream of the synthesis gas compressor in terms of process technology. In other words, before the line arrangement is switched, the H-recycling flow is supplied to the synthesis gas flow and said supply to the synthesis gas flow takes place upstream of the synthesis gas compressor in terms of process technology. In this way, the H-recycling flow experiences, together with the synthesis gas flow, a pressure increase through the synthesis gas compressor and the recovery flow can be supplied to the hydrogen recovery arrangement at a comparatively low pressure.

According to a further preferred embodiment of the method, it is preferred that, by switching the line arrangement, the hydrogen of the H-recycling flow is supplied to the methanol reactor arrangement at an increased pressure for partial conversion to methanol. The pressure of the hydrogen is then increased with respect to the pressure of the hydrogen without switching the line arrangement. In other words, it is preferred that, by switching the line arrangement, the hydrogen of the H-recycling flow is supplied to the methanol reactor arrangement at a higher pressure than before the line arrangement was switched. This applies particularly upon failure of the synthesis gas compressor. The H-recycling flow, particularly as a whole, by switching the line arrangement, is preferably supplied to the methanol reactor arrangement at a higher pressure than before the line arrangement was switched.

Such an increased pressure can, on the one hand, be brought about by the fact that the H-recycling flow experiences a direct pressure increase or an indirect pressure increase. As already stated, an indirect increase in pressure can be achieved, for example, by increasing the pressure of the recovery flow. However, it can also be that the hydrogen is then supplied to the methanol reactor arrangement at an increased pressure even if the H-recycling flow itself does not experience any increase in pressure.

A preferred embodiment of the method is characterized in that the synthesis gas flow is obtained in a synthesis gas reactor arrangement of the plant from a carbon-containing energy carrier flow. The synthesis gas reactor arrangement can have further devices in addition to a reactor for generating the synthesis gas. The synthesis gas reactor arrangement can thus have a device upstream of the reactor in terms of process technology for desulfurization of the carbon-containing energy carrier flow, a saturation stage for saturating the carbon-containing energy carrier flow with water, a pre-reformer for pre-reforming the carbon-containing energy carrier flow and/or a device for heating the carbon-containing energy carrier flow.

In principle, the synthesis gas flow can be obtained in any desired manner. It is preferred that an oxygen-containing flow is supplied to the synthesis gas reactor arrangement in order to obtain the synthesis gas flow. In principle, the oxygen-containing flow can also comprise further constituents in addition to the oxygen. The oxygen-containing flow can also be ambient air. Furthermore, it can be that before the switching, the H-recycling flow is supplied to the synthesis gas flow downstream of the synthesis gas reactor arrangement in terms of process technology. When the synthesis gas compressor is functioning, it is more expedient not to direct the recovered hydrogen through the synthesis gas reactor arrangement.

In principle, the synthesis gas flow can be obtained, for example, by steam reforming the carbon-containing energy carrier flow. A further preferred embodiment of the method is characterized in that in the synthesis gas reactor arrangement, the synthesis gas flow is obtained from the carbon-containing energy carrier flow by autothermal reforming. In such an autothermal reforming, a catalytic partial oxidation provides the heat required for the endothermic reforming reactions. Compared to pure steam reforming, autothermal reforming offers the advantage that the synthesis gas flow can be provided at a higher pressure.

In principle, such an autothermal reforming can also be operated with ambient air. However, it is preferred that the oxygen-containing flow is obtained from an air separation device for obtaining an oxygen flow from ambient air. The air separation device can furthermore also be set up to obtain a nitrogen flow. Particularly, it can then be that the oxygen-containing flow consists essentially of oxygen. In this way, the proportion of inert gases in the methanol synthesis is reduced, so that, among other things, compressors and other devices in the plant can be dimensioned smaller.

According to a preferred embodiment of the method, it is provided that after the line arrangement has been switched, the H-recycling flow is supplied to the energy carrier flow. Particularly, after the line arrangement has been switched, the H-recycling flow is supplied to the energy carrier flow upstream of the synthesis gas reactor arrangement in terms of process technology. In this way, the pressure reached in an autothermal reforming process can also be extended to the hydrogen of the H-recycling flow. It can also be that the plant has an energy carrier compressor for increasing the pressure of the energy carrier flow before it is supplied to the synthesis gas reactor arrangement and that after the line arrangement has been switched, the H-recycling flow is supplied to the energy carrier flow upstream of the energy carrier compressor. In this way, the hydrogen in the H-recycling flow can also experience a pressure increase through the energy carrier compressor.

In addition to the H-recycling flow, the hydrogen recovery arrangement can also output further flows. The hydrogen recovery arrangement preferably outputs a purge flow. Said purge flow can particularly be discharged for combustion.

In principle, the H-recycling flow can comprise any composition as long as said H-recycling flow contains hydrogen. According to a further preferred embodiment of the method, it is provided that the H-recycling flow has a higher molar proportion of hydrogen than the recovery flow. In other words, the hydrogen in the H-recycling flow is enriched with respect to the recovery flow. It is also preferred that the H-recycling flow comprises a higher molar proportion of hydrogen than the purge flow.

In principle, the hydrogen recovery arrangement can function according to any desired principle, for example, based on a membrane or a refrigeration device. A preferred embodiment of the method is characterized in that the hydrogen recovery arrangement has a pressure swing adsorption device (PSA) for obtaining the H-recycling flow from the recovery flow. A high level of hydrogen recovery can be achieved in the H-recycling flow in this way. A high hydrogen purity is actually not required but can be achieved. It can therefore be that the H-recycling flow consists essentially of hydrogen.

The proposed plant is used for synthesizing methanol. Said plant has a synthesis gas compressor to which a synthesis gas flow comprising hydrogen and carbon oxides is supplied to increase the pressure of the synthesis gas flow, a methanol reactor arrangement to which the pressure-increased synthesis gas flow is supplied for partial conversion to methanol and a hydrogen recovery arrangement for obtaining an H-recycling flow comprising hydrogen from a recovery flow supplied by the methanol reactor arrangement, wherein the hydrogen is at least in part converted to methanol.

The proposed plant is characterized in that the plant has a line arrangement and a switching arrangement, which switching arrangement switches the line arrangement upon failure of the synthesis gas compressor such that the H-recycling flow is adjusted to compensate for a pressure loss in the methanol reactor arrangement.

Features, advantages and properties of the proposed plant correspond to the features, advantages and properties of the proposed method and vice versa.

BRIEF DESCRIPTION OF THE DRAWINGS

Further details, features, objectives and advantages of the present disclosure are explained below with reference to the drawing, which shows only exemplary embodiments. The drawing shows.

DETAILED DESCRIPTION OF THE DRAWINGS

Figure 1:
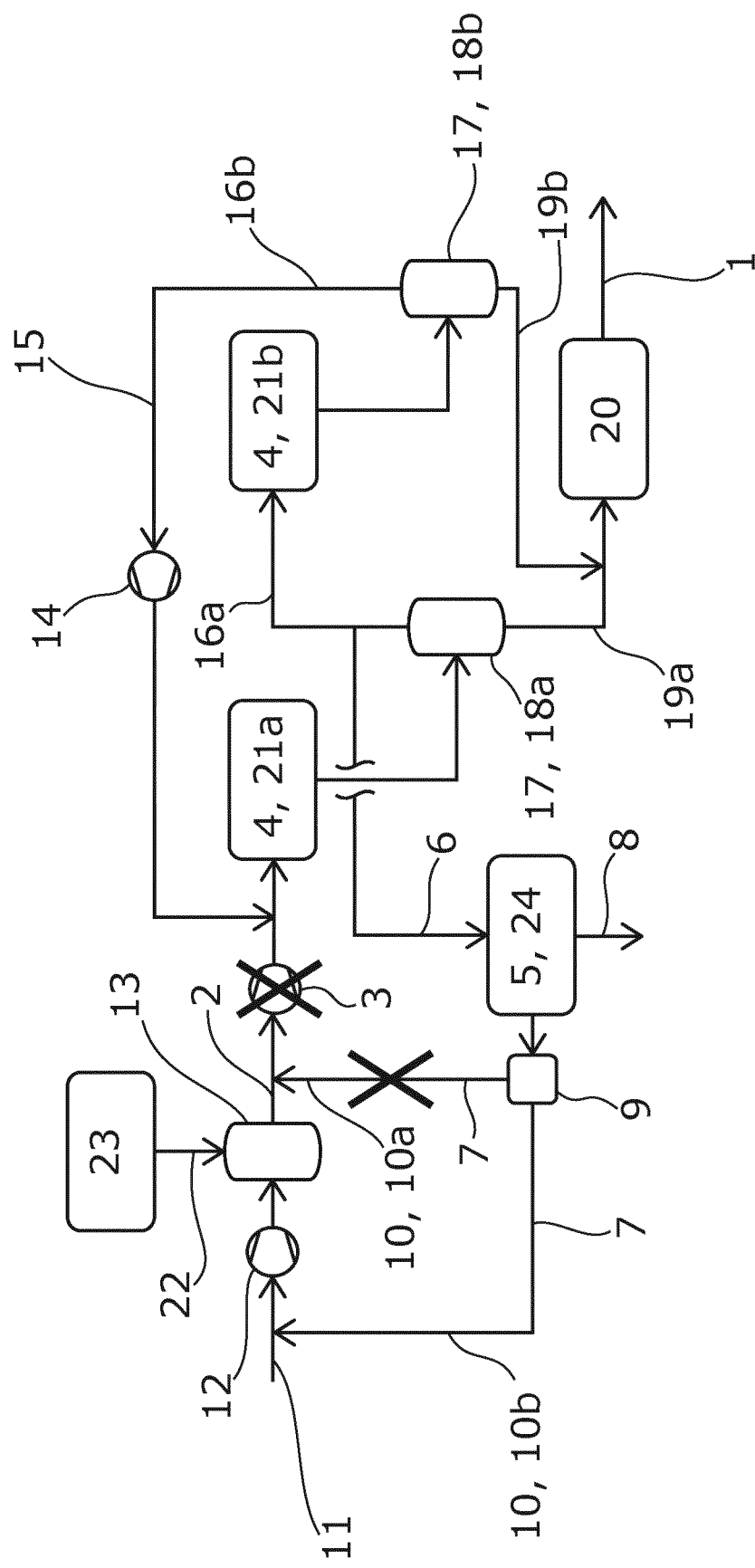
FIG. 1 schematically the flow diagram of a plant for carrying out the proposed method according to a first embodiment, FIG. 2 schematically the flow diagram of a plant for carrying out the proposed method according to a second embodiment, FIG. 3 schematically the flow diagram of a plant for carrying out the proposed method according to a third embodiment, FIG. 4 schematically the flow diagram of a plant for carrying out the proposed method according to a fourth embodiment, FIG. 5 schematically the flow diagram of a plant for carrying out the proposed method according to a fifth embodiment, FIG. 6 schematically the flow diagram of a plant for carrying out the proposed method according to a sixth embodiment, and FIG. 7 schematically the flow diagram of a plant for carrying out the proposed method according to a seventh embodiment.

The plant shown in FIG. 1 according to a first embodiment of the proposed plant is used for synthesizing methanol 1 and can be operated according to the proposed method.

A synthesis gas flow 2 consisting essentially of hydrogen, carbon monoxide and carbon dioxide is supplied to a synthesis gas compressor 3 of the plant, which synthesis gas compressor 3 compresses the synthesis gas flow 2 to a desired pressure for synthesizing methanol and then supplies to a methanol reactor arrangement 4 in which a methanol synthesis takes place and at least part of the synthesis gas flow 2 is converted to methanol 1.

The plant has a pressure swing adsorption system 24, which can also be referred to as a PSA, formed hydrogen recovery arrangement 5, which obtains an H-recycling flow 7 from a recovery flow 6 from the methanol reactor arrangement 4, which recovery flow 6 consists essentially of hydrogen. Likewise, the remaining gas is output from the hydrogen recovery arrangement 5 as a purge flow 8 and then burned in a fired heating device of the plant (not shown here).

In normal operation, that is, with a functioning synthesis gas compressor 3, the H-recycling flow 7 is supplied to the synthesis gas flow 2, to be precise, upstream of the synthesis gas compressor 3. The synthesis gas compressor 3 also compresses the hydrogen in the H-recycling flow 7 in this way and supplies it to the methanol reactor arrangement 4.

The synthesis gas flow 2 is obtained from an energy carrier flow 11 formed by natural gas and thus containing carbon, which energy carrier flow 11 is first supplied to an energy carrier compressor 12 and, after the corresponding pressure increase, to a synthesis gas reactor arrangement 13. An autothermal reforming takes place in the synthesis gas reactor arrangement 13 in order to obtain the synthesis gas flow 2. An oxygen-containing flow 22 is supplied for the autothermal reforming, which oxygen-containing flow 22 was obtained here from an air separation device 23 and consists essentially of oxygen. The air separation device 23 is set up to obtain an oxygen flow, in this case the oxygen-containing flow 22, from the ambient air.

The plant and particularly the methanol reactor arrangement 4 continue to be operated after a failure of the synthesis gas compressor 3. To compensate for the failure of the synthesis gas compressor 3, a switching arrangement 9 of the plant switches the line arrangement 10, which directs the H-recycling flow 7 so that the H-recycling flow 7 is supplied to the energy carrier flow 11 following failure of the synthesis gas compressor 3 and after the switching. Specifically, said supply takes place upstream of both the synthesis gas reactor arrangement 13 and the energy carrier compressor 12 in terms of process technology. FIG. 1 shows both the sub-line 10a of the line arrangement 10 used before the switching to direct the H-recycling flow 7 and the sub-line 10b of the line arrangement 10 used following failure of the synthesis gas compressor 3 and after the switching to direct the H-recycling flow 7.

Due to the energy carrier compressor 12, the hydrogen in the H-recycling flow 7 experiences a pressure increase after the switching with respect to the state before the switching, which pressure increase at least partially compensates for the pressure loss in the methanol reactor arrangement 4 from the failure of the synthesis gas compressor 3.

As can be seen in FIG. 1, the plant of the first embodiment also has a recycle compressor 14 which compresses a residual gas flow 15. The residual gas flow 15 comprises unreacted residual gas 16b, which in turn essentially comprises those constituents of the synthesis gas which were not converted to methanol 1 in the methanol reactor arrangement 4. The residual gas flow 15, which is thus increased in pressure, is supplied to the methanol reactor arrangement 4 again.

The unreacted residual gas 16a, b is obtained from a methanol separation device 17 of the methanol reactor arrangement 4, which here comprises two condensation devices 18a, b. The unreacted residual gas 16a, b, on the one hand, and a respective crude methanol flow 19a, b on the other hand, are obtained in each of these by condensation. The crude methanol flows 19a, b are then supplied to a distillation 20 of the plant, so that the methanol 1 can be obtained from the crude methanol flows 19a, b.

In the plant of the embodiment of FIG. 1, the methanol reactor arrangement 4 has two reactor stages 21a, b connected in series in terms of process technology for synthesizing methanol. In this embodiment, the first reactor stage 21a has two isothermal reactors arranged parallel to one another and the second reactor stage 21b has a single isothermal reactor. The product flow from a respective reactor stage 21a, b is supplied to each of the two condensation devices 18a, b. That reactor stage 21a to which the synthesis gas flow 1 is supplied directly is referred to as the first reactor stage 21a. The reactor stage 21b is then downstream of first reactor stage 21a in terms of process technology in that the unreacted residual gas 16a from the first reactor stage 21a is supplied thereto for conversion to methanol 1.

In this embodiment of FIG. 1, the recovery flow 6 is branched off from the unreacted residual gas 16a of the first reactor stage 21a. In contrast, the residual gas flow 15 supplied to the recycle compressor 14 is not obtained from said unreacted residual gas 16a of the first reactor stage 21a, but rather from the unreacted residual gas 16b of the reactor stage 21b downstream of the first reactor stage 21a. The residual gas flow 15 compressed by the recycle compressor 14 is then in turn supplied to the first reactor stage 21a.

Figure 2:
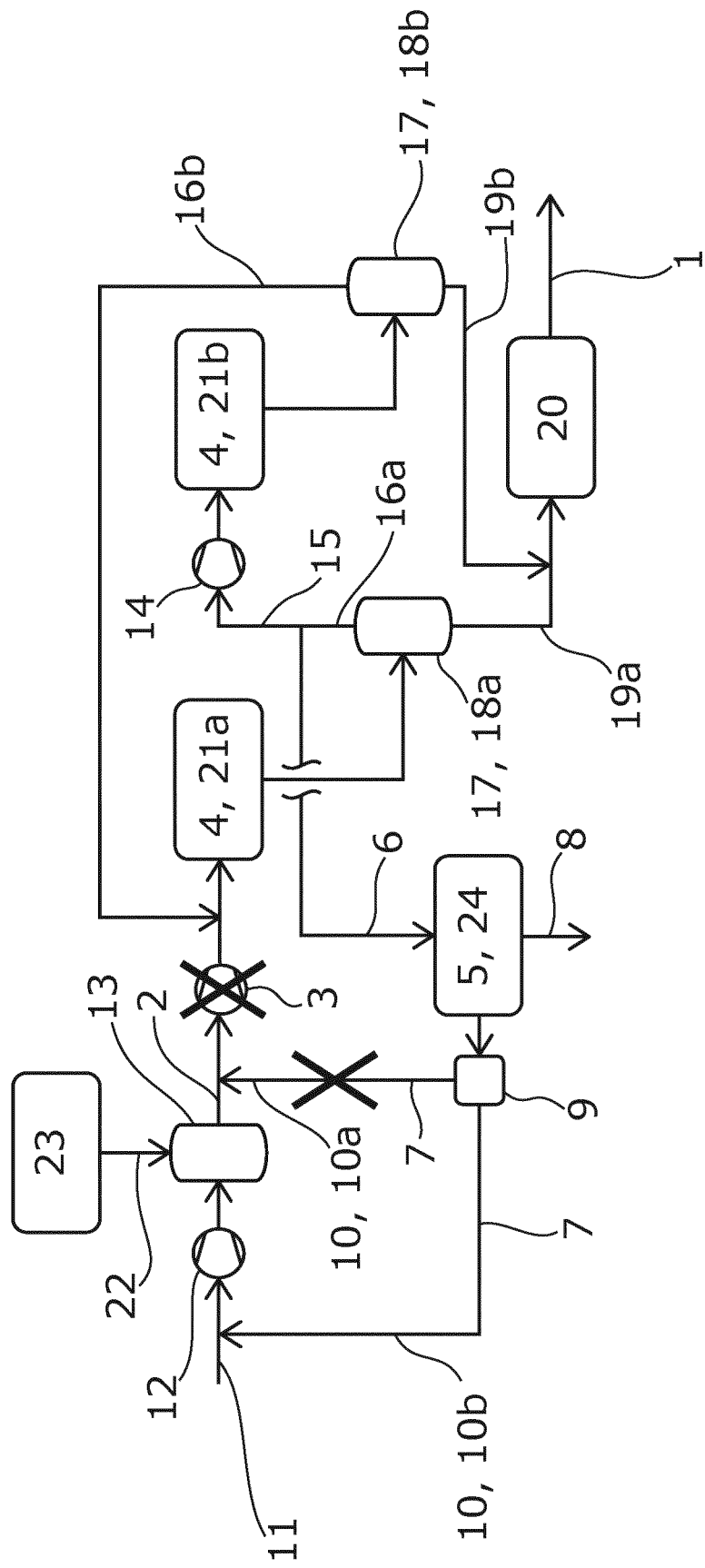

The second embodiment of the proposed plant, shown in FIG. 2, differs from the embodiment in FIG. 1 only in that the recycle compressor 14 is arranged in terms of process technology between the first reactor stage 21a and the reactor stage 21b downstream thereof. Consequently, the residual gas flow 15 supplied to the recycle compressor 14 is obtained from the unreacted residual gas 16a of the first reactor stage 21a. The residual gas flow 15 compressed by the recycle compressor 14 is supplied to the reactor stage 21b downstream of the first reactor stage 21a. The unreacted residual gas 16b from said reactor stage 21b is supplied back to the first reactor stage 21a without further compression. As in the first embodiment, the recovery flow 6 is obtained from the unreacted residual gas 16a of the first reactor stage 21a, wherein the branching off of the recovery flow 6 takes place upstream of the recycle compressor 14 in terms of process technology.

Figure 3:
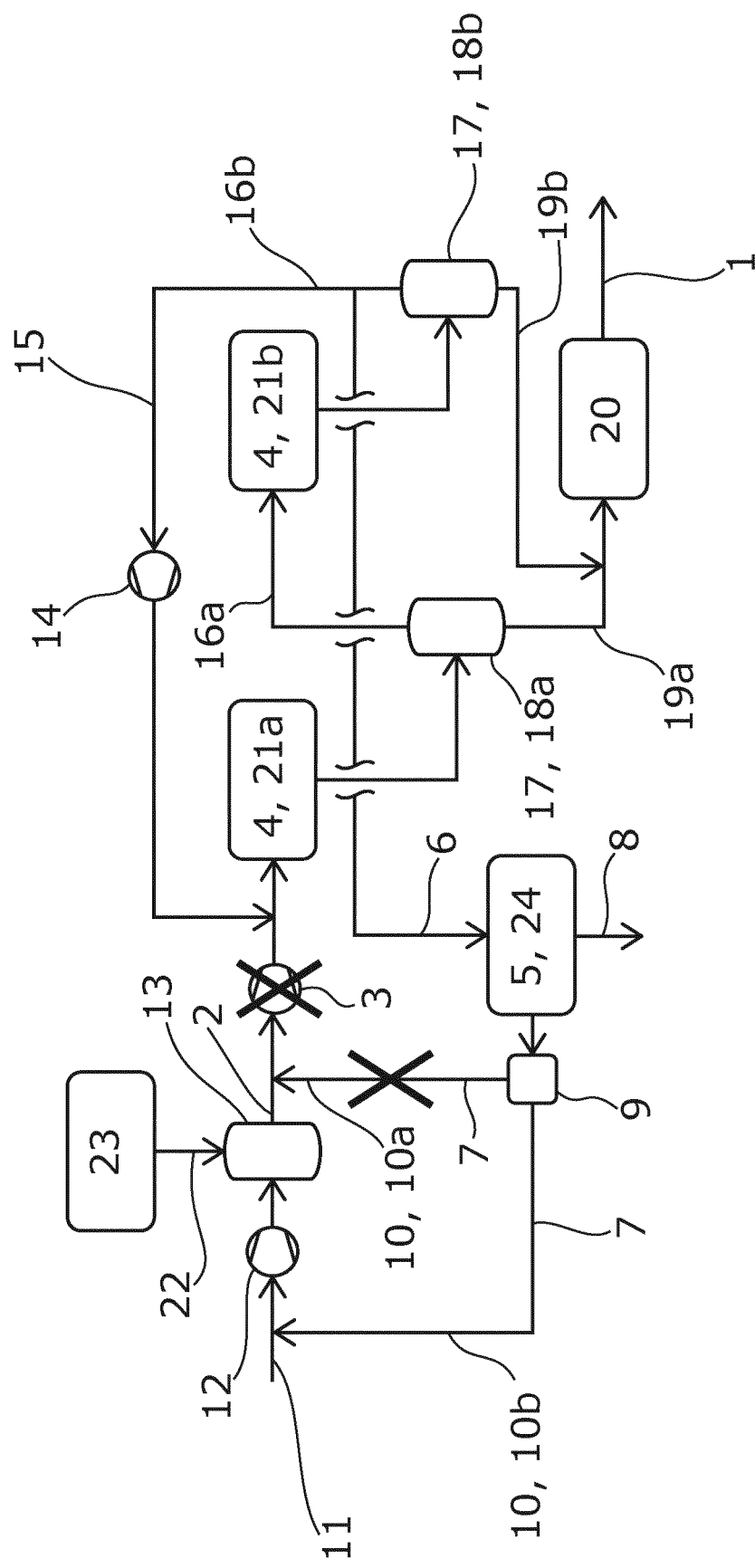

The third embodiment of the proposed plant of FIG. 3 corresponds to the first embodiment of FIG. 1, with the difference that the residual gas flow 6 is obtained from the unreacted residual gas 16b of the reactor stage 21b downstream of the first reactor stage 21a. The branching-off of the residual gas flow 6 takes place upstream of the recycle compressor 14 in terms of process technology.

Figure 4:
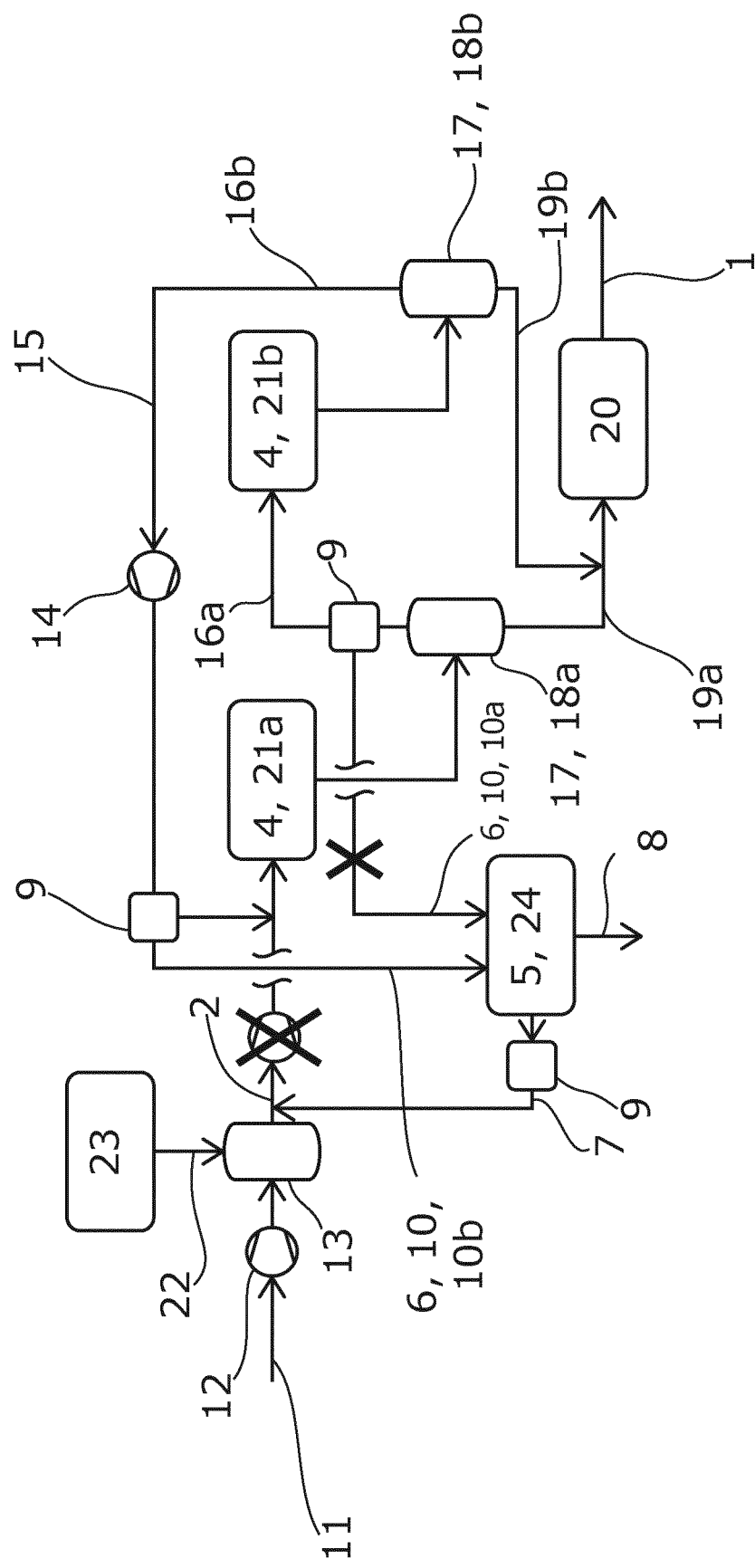

The fourth embodiment of the proposed plant of FIG. 4 corresponds to the first embodiment of FIG. 1 in the state with the synthesis gas compressor 3 in operation. Upon failure of the synthesis gas compressor 3, however, in contrast to the embodiments in FIGS. 1 to 3, the switching does not change the course of the H-recycling flow 7, but rather changes the course of the recovery flow 6. By switching the line arrangement 10, the recovery flow 6 is no longer branched off through the sub-line 10a of the line arrangement 10 and thus no longer from the unreacted residual gas 16a of the first reactor stage 21a, but rather from the residual gas flow 15, which is pressure-increased by the recycle compressor 14, and thus through the sub-line 10b of the line arrangement 10. Because the recovery flow 6 experiences a pressure increase through the recycle compressor 14 after the switching, the recovery flow 6 is therefore supplied to the hydrogen recovery arrangement 5 at a higher pressure than before the switching. However, this also results in a pressure increase in the H-recycling flow 7, even if the supply of the H-recycling flow 7 per se remains unchanged.

Figure 5:
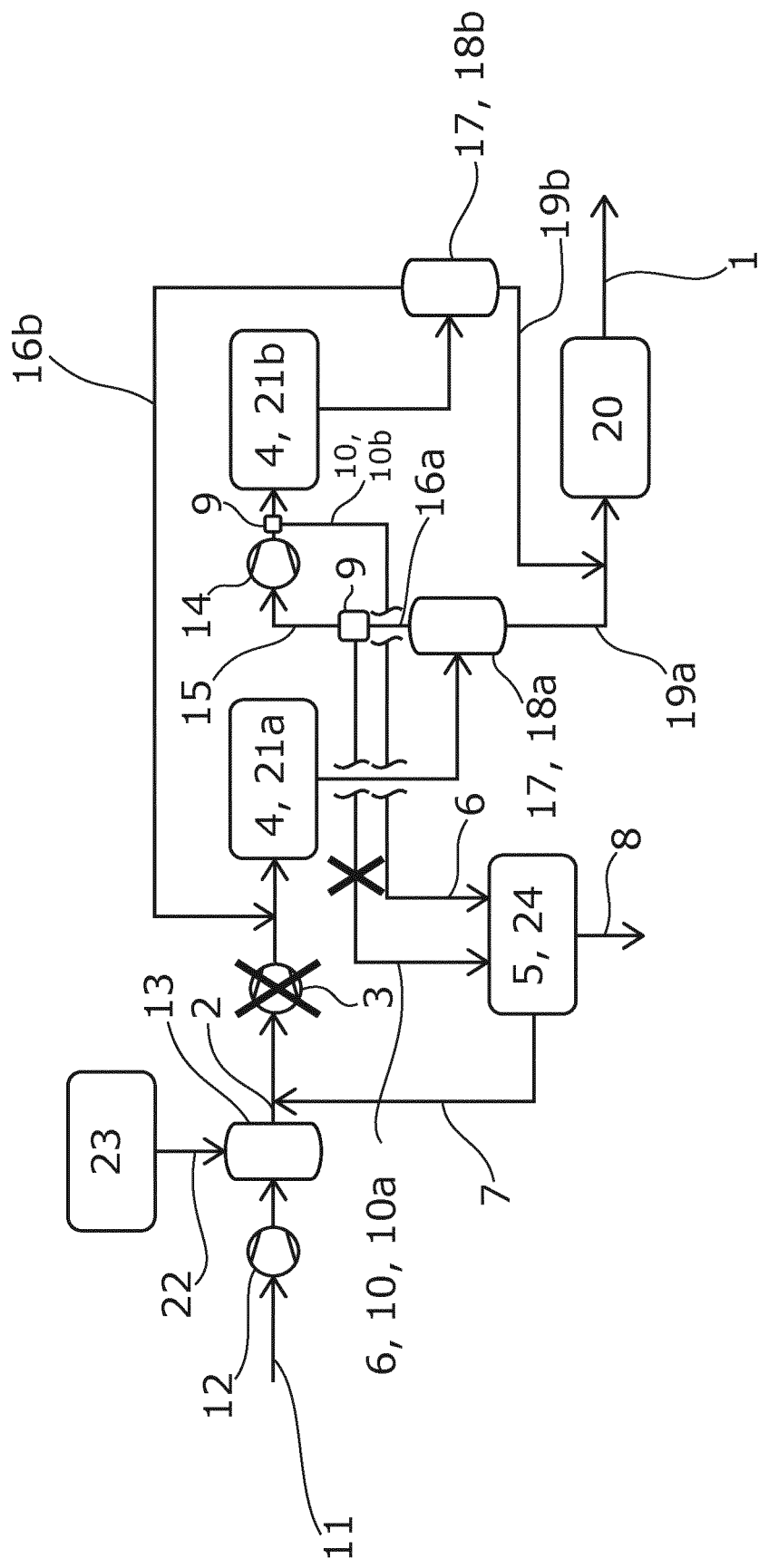

The fifth embodiment of the proposed plant of FIG. 5 behaves in a manner analogous to the second embodiment of FIG. 2 as does the fourth embodiment of FIG. 4 in relation to the first embodiment of FIG. 1. Particularly, the state with the operation of the synthesis gas compressor 3 of the plant of FIG. 5 is identical to the state with the operation of the synthesis gas compressor 3 of the plant of FIG. 2. Upon failure of the synthesis gas compressor 3, unlike in the plant of FIG. 2, the supply of the H-recycling flow 7 is not changed by switching, but rather that of the recovery flow 6. After the line arrangement 10 has been switched, the recovery flow 6 is no longer branched off from the unreacted residual gas 16a of the first reactor stage 21a before the pressure increase, but rather from the residual gas flow 15 which has been pressure-increased by the recycle compressor 14. The changed supply again corresponds to the first sub-line 10a of the line arrangement 10 before the switching and the second sub-line 10b of the line arrangement after the switching.

Since the recycle compressor 14 is arranged in terms of process technology between the first reactor stage 21a and the reactor stage 21b downstream thereof, the recovery flow 6 is thus branched off in terms of process technology after the pressure increase by the recycle compressor 14 and before being supplied to the reactor stage 21b downstream of the first reactor stage 21a. As in the embodiment of FIG. 4, this results in an increase in pressure of the recovery flow 6 supplied to the hydrogen recovery arrangement 5.

Figure 6:
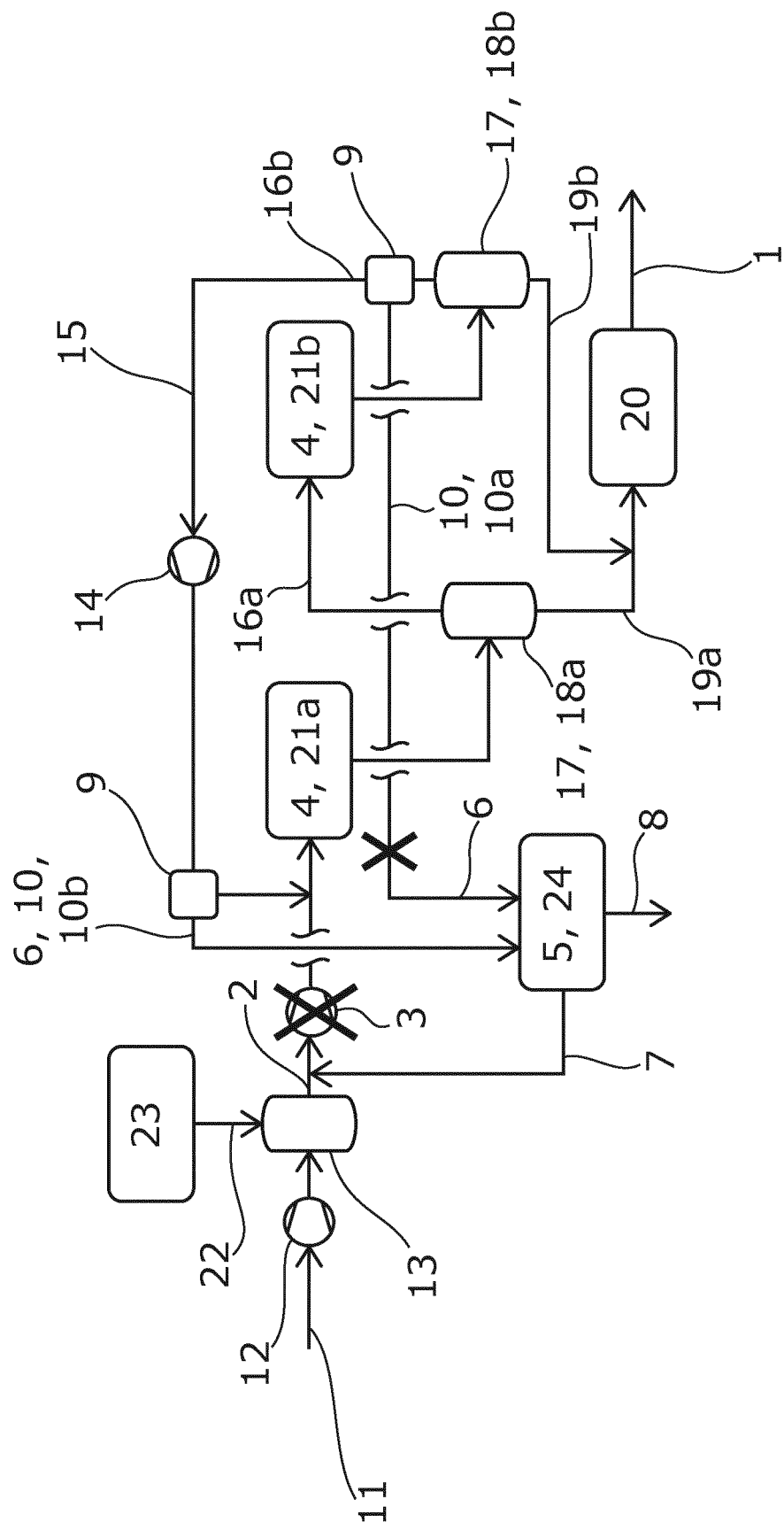

The sixth embodiment of the proposed plant of FIG. 6, in turn, relates to the third embodiment of FIG. 3, analogously to the fourth embodiment of FIG. 4 to that of FIG. 1 and the fifth embodiment of FIG. 5 to that of FIG. 2. This means that the state with the operation of the synthesis gas compressor 3 of the plant of FIG. 6 is identical to the state with the operation of the synthesis gas compressor 3 of the plant of FIG. 3.

Upon failure of the synthesis gas compressor 3, unlike in the plant of FIG. 3, the supply of the H-recycling flow 7 is not changed by switching, but rather that of the recovery flow 6. After the line arrangement 10 has been switched, the recovery flow 6 is no longer branched off from the unreacted residual gas 16b of the reactor stage 21b downstream of the first reactor stage 21a, but rather from the residual gas flow 15, which is pressure-increased by the recycle compressor 14. Since the arrangement of the recycle compressor 14 corresponds to that of the embodiment of FIG. 4, the recovery flow 6 is thus also here branched off in terms of process technology after the pressure increase by the recycle compressor 14 and before being supplied to the first reactor stage 21a. As in the embodiment of FIG. 4, this likewise results in a pressure increase in the recovery flow 6 supplied to the hydrogen recovery arrangement 5.

Figure 7:
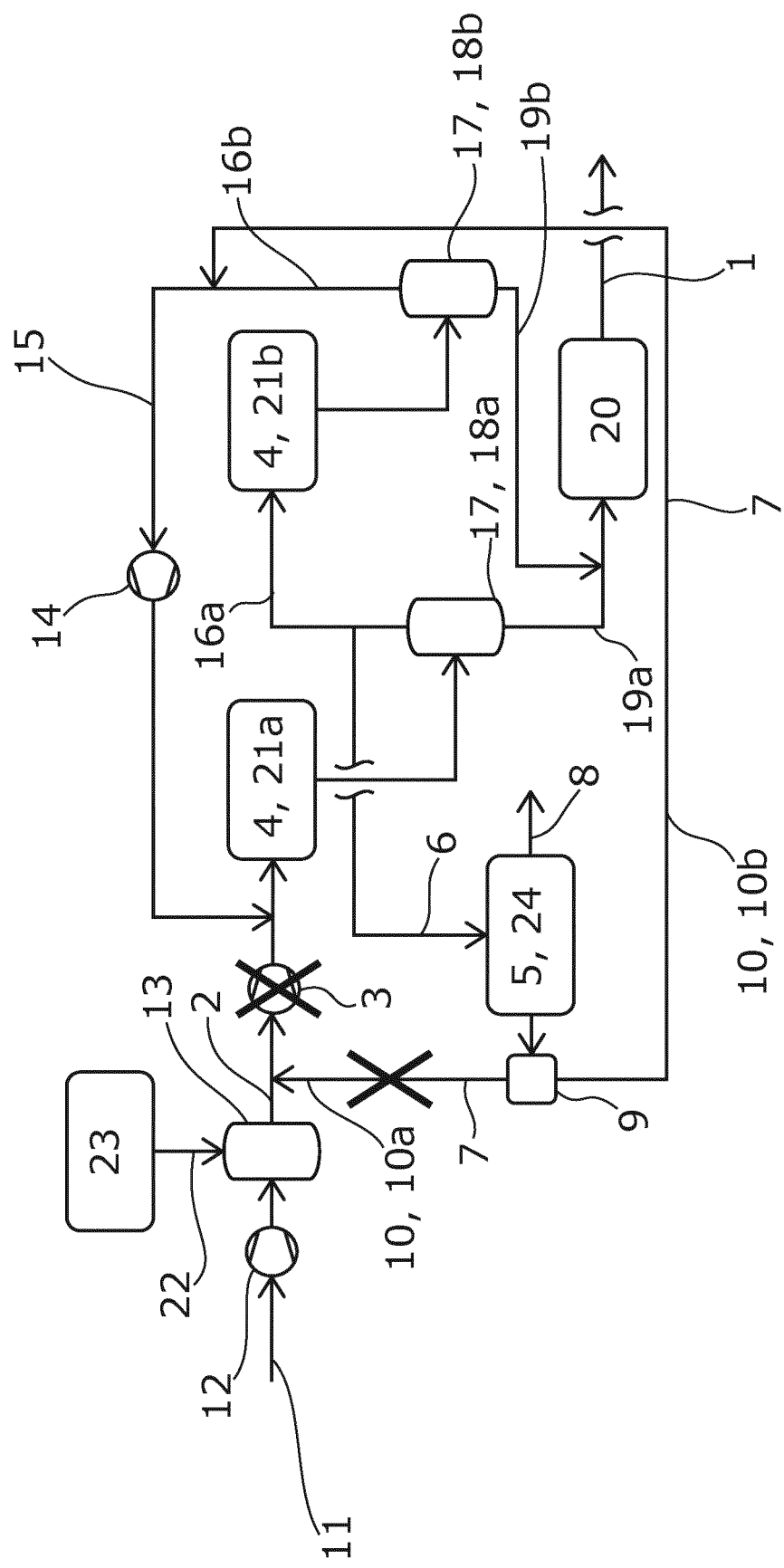

Finally, the seventh embodiment of the proposed plant of FIG. 7 again corresponds to the first embodiment of FIG. 1 in the state with the synthesis gas compressor 3 in operation. As in the embodiment of FIG. 1, in the embodiment of FIG. 7, upon failure of the synthesis gas compressor 3, the switching also changes the supply of the H-recycling flow 7. In fact, after the switching, the H-recycling flow 7 is supplied to the residual gas flow 15, which here is obtained from the residual gas 16b of the reactor stage 21b downstream of the first reactor stage 21a. Particularly, said supply takes place before the pressure increase by the recycle compressor 14. In this way, the hydrogen in the H-recycling flow 7 receives a pressure increase through the recycle compressor 14, which at least in part compensates for the lack of pressure increase due to the failure of the synthesis gas compressor 3.

The invention claimed is:

1. A method for operating a plant for synthesizing methanol, a synthesis gas flow comprising hydrogen and carbon oxides being supplied to a synthesis gas compressor of the plant to increase the pressure of the synthesis gas flow, the pressure-increased synthesis gas flow being supplied to a methanol reactor arrangement of the plant for partial conversion to methanol and the plant having a hydrogen recovery arrangement which obtains an H-recycling flow comprising hydrogen from a recovery flow supplied from the methanol reactor arrangement, which hydrogen is converted at least in part to methanol, wherein upon failure of the synthesis gas compressor, the synthesis gas flow continues to be supplied to the methanol reactor arrangement for partial conversion to methanol and that, following failure of the synthesis gas compressor, a line arrangement of the plant is switched such that the H-recycling flow is adjusted to compensate for a pressure loss in the methanol reactor arrangement.

2. The method according to claim 1, wherein a residual gas flow comprising unreacted residual gas is obtained from the methanol reactor arrangement and that the plant has a recycle compressor for increasing the pressure of the residual gas flow and for supplying the pressure-increased residual gas flow to the methanol reactor arrangement for partial conversion to methanol, that the methanol reactor arrangement comprises a methanol separation device for obtaining the unreacted residual gas and a crude methanol flow, wherein the methanol separation device comprises a condensation device for obtaining the unreacted residual gas and the crude methanol flow by condensation.

3. The method according to claim 2, wherein the methanol reactor arrangement has a plurality of reactor stages connected in series in terms of process technology for synthesizing methanol, wherein the recycle compressor is arranged between two reactor stages in terms of process technology.

4. The method according to claim 3, wherein the pressure-increased synthesis gas flow is supplied to a first reactor stage of the plurality of reactor stages, wherein the residual gas flow is obtained from a reactor stage downstream of the first reactor stage in terms of process technology, wherein the recycle compressor supplies the pressure-increased residual gas flow to the first reactor stage.

5. The method according to claim 2, wherein after the line arrangement has been switched, the H-recycling flow is supplied to the unreacted residual gas, wherein the H-recycling flow together with the residual gas flow is supplied to the recycle compressor to increase the pressure.

6. The method according to claim 1, wherein the course of the recovery flow is changed by switching the line arrangement, wherein before the line arrangement is switched, the recovery flow is branched off from the unreacted residual gas, upstream of the recycle compressor in terms of process technology.

7. The method according to claim 1, that by switching the line arrangement, the recovery flow is supplied to the hydrogen recovery arrangement at an increased pressure, wherein by switching the line arrangement, the recovery flow is supplied to the line arrangement at a higher pressure than before the switching, wherein after the switching of the line arrangement, the recovery flow is branched off from the residual gas flow downstream of the recycle compressor.

8. The method according to claim 1, wherein by switching the line arrangement, the course of the H-recycling flow is changed, wherein before the switching of the line arrangement, the H-recycling flow is supplied to the synthesis gas flow upstream of the synthesis gas compressor in terms of process technology.

9. The method according to claim 1, wherein by switching the line arrangement, the hydrogen of the H-recycling flow is supplied to the methanol reactor arrangement at an increased pressure for partial conversion to methanol, wherein by switching the line arrangement, the hydrogen of the H-recycling flow, is supplied to the methanol reactor arrangement at a higher pressure than, particularly following failure of the synthesis gas compressor, before the switching of the line arrangement.

10. The method according to claim 1, wherein the synthesis gas flow is obtained in a synthesis gas reactor arrangement of the plant from a carbon-containing energy carrier flow, wherein an oxygen-containing flow is supplied to the synthesis gas reactor arrangement for obtaining the synthesis gas flow, wherein before the switching, the H-recycling flow is supplied to the synthesis gas flow downstream of the synthesis gas reactor arrangement in terms of process technology.

11. The method according to claim 10, wherein in the synthesis gas reactor arrangement, the synthesis gas flow is obtained by autothermal reforming from the carbon-containing energy carrier flow, wherein the oxygen-containing flow is obtained from an air separation device for obtaining an oxygen flow from an ambient air, wherein the oxygen-containing flow comprises oxygen.

12. The method according to claim 10, wherein after the line arrangement has been switched, the H-recycling flow is supplied to the energy carrier flow, upstream of the synthesis gas reactor arrangement in terms of process technology, further that the plant has an energy carrier compressor to increase the pressure of the energy carrier flow before it is supplied to the synthesis gas reactor arrangement and that, after the line arrangement has been switched, the H-recycling flow is supplied to the energy carrier flow upstream of the energy carrier compressor, further that the hydrogen recovery arrangement outputs a purge flow which is further discharged, for combustion.

13. The method according to claim 1, wherein the H-recycling flow has a higher molar proportion of hydrogen than the recovery flow.

14. The method according to claim 1, wherein the hydrogen recovery arrangement has a pressure swing adsorption device for obtaining the H-recycling flow from the recovery flow, further that the H-recycling flow comprises hydrogen.

15. A plant for synthesizing methanol having a synthesis gas compressor, to which a synthesis gas flow comprising hydrogen and carbon oxides is supplied to increase the pressure of the synthesis gas flow, having a methanol reactor arrangement, to which the pressure-increased synthesis gas flow is supplied for partial conversion to methanol and having a hydrogen recovery arrangement for obtaining an H-recycling flow comprising hydrogen from a recovery flow supplied by the methanol reactor arrangement (4), the hydrogen at least in part being converted to methanol, wherein the plant has a line arrangement and a switching arrangement which, upon failure of the synthesis gas compressor, switches the line arrangement such that the H-recycling flow is adjusted to compensate for a pressure loss in the methanol reactor arrangement.

* * * * *